(12) United States Patent
Yao et al.

(10) Patent No.: US 6,673,974 B1
(45) Date of Patent: Jan. 6, 2004

(54) PROCESS FOR PRODUCTION OF 1,1-BIS(4-HYDROXYPHENYL)-3,3,5-TRIMETHYLCYCLOHEXANE

(75) Inventors: Kazuhiko Yao, Wakayama (JP); Kenji Ekawa, Wakayama (JP); Yoichiro Isota, Wakayama (JP); Toru Nakaguchi, Wakayama (JP)

(73) Assignee: Honshu Chemical Industry Co. Ltd., Tokyo (JP)

( * ) Notice: Subject to any disclaimer, the term of this patent is extended or adjusted under 35 U.S.C. 154(b) by 0 days.

(21) Appl. No.: 10/363,706
(22) PCT Filed: Sep. 11, 2000
(86) PCT No.: PCT/JP00/06206
§ 371 (c)(1), (2), (4) Date: Mar. 6, 2003
(87) PCT Pub. No.: WO02/22535
PCT Pub. Date: Mar. 21, 2002
(51) Int. Cl.$^7$ ................................................. C07C 39/17
(52) U.S. Cl. ...................................................... 568/721
(58) Field of Search .......................................... 568/721

(56) References Cited

U.S. PATENT DOCUMENTS

| 5,227,458 A | * | 7/1993 | Freitag |
| 5,336,812 A | * | 8/1994 | Salek |
| 5,783,733 A | * | 7/1998 | Kissinger |
| 6,284,931 B1 | * | 9/2001 | Isota |

FOREIGN PATENT DOCUMENTS

| EP | 995737 | * | 4/2000 |

* cited by examiner

Primary Examiner—Michael L. Shippen
(74) Attorney, Agent, or Firm—Merchant & Gould P.C.

(57) ABSTRACT

A process for production of 1,1-bis(4-hydroxyphenyl)-3,3,5-trimethylcyclohexane which comprises reacting phenol with 3,3,5-trimethylcyclohexanone in the presence of an acid catalyst wherein the reaction of phenol with 3,3,5-trimethylcyclohexanone is started in a slurry comprising phenol adduct crystals of 1,1-bis(4-hydroxyphenyl)-3,3,5-trimethylcyclohexane and hydrated phenol in the presence of an acid catalyst, and then the reaction is continued in the slurry.

3 Claims, No Drawings

PROCESS FOR PRODUCTION OF 1,1-BIS(4-HYDROXYPHENYL)-3,3,5-TRIMETHYLCYCLOHEXANE

TECHNICAL FIELD

The invention relates to a process for production of 1,1-bis(4-hydroxyphenyl)-3,3,5-trimethylcyclohexane (referred to as "BPTMC" hereinafter) in high yield and in high selectivity by an acid condensation reaction of phenol with 3,3,5-trimethylcyclohexanone (referred to as "TMC" hereinafter) in a stable manner.

BACKGROUND ART

In recent years, BPTMC is used as raw materials for the production of optical products such as optical disks, as well as synthetic resins for optical use such as polycarbonate resins for optical use. A variety of processes for the production of BPTMC are already known. According to one of such processes, phenol is reacted with TMC using hydrogen chloride gas as a catalyst and an alkyl mercaptan as a promoter in the presence of an inactive organic solvent or in the absence of a solvent and then phenol remained unreacted is removed from the reaction mixture by steam distillation, as described in Japanese Patent Application Laid-open No. 2-88634. It is also described therein that, after the reaction, water is added to the reaction mixture, and then an alkali to neutralize the reaction mixture, followed by heating, cooling and removing an aqueous phase, thereby obtaining the desired BPTMC as residue.

A further process is known, as is described in Japanese Patent Application Laid-open No. 8-505644. According to the process, phenol is reacted with TMC using hydrogen chloride gas as a catalyst and an alkyl mercaptan such as octanethiol as a promoter. After the reaction, water is added to the reaction mixture to form a slurry, and the slurry is filtered to provide 1:1 adduct crystals of BPTMC and phenol, and then the phenol is removed from the adduct crystals, thereby providing the desired BPTMC.

A process is also known, as described in Japanese Patent Application Laid-open No. 4-282334. The process provides the desired BPTMC by the reaction of phenol with TMC using water-insoluble cation exchange resins having sulfonic acid groups therein as a catalyst and a mercaptan compound as a promoter. In Japanese Patent Application Laid-open No. 5-213803, there is described a process in which an acid catalyst such as benzenesulfonic acid is added to a mixture of phenol, TMC, a mercaptan compound as a promoter and water, whereupon the reaction is started with stirring, and the desired BPTMC is obtained in high selectivity.

As mentioned hereinbefore, BPTMC is used as raw materials for polycarbonate resins for optical use. In order to supply BPTMC to this use, it is more and more strongly demanded to produce high purity BPTMC which is free of by-products derived from the reaction, and besides free of high boiling point by-products or colored by-products derived from purification processes for the obtained reaction product and residual phenol or trace impurities such as sodium.

It is essentially important to increase the selectivity and yield of the reaction to produce the desired high purity and high quality product in a stable manner. However, according to the known processes for production of BPTMC by the condensation reaction of phenol with TMC in the presence of an acid catalyst, the selectivity of reaction is so small as about 70% so long as the present inventors know.

The invention has been accomplished to solve such problems as involved in the known processes for the production of BPTMC by an acid condensation reaction of phenol and TMC. Therefore, it is an object of the invention to provide a process suitable for industrial production of BPTMC in high selectivity and in high yield in a stable manner.

SUMMARY OF THE INVENTION

The invention provides a process for production of 1,1-bis(4-hydroxyphenyl)-3,3,5-trimethylcyclohexane which comprises reacting phenol with 3,3,5-trimethylcyclohexanone in the presence of an acid catalyst wherein the reaction of phenol with 3,3,5-trimethylcyclohexanone is started in a slurry comprising phenol adduct crystals of 1,1-bis(4-hydroxyphenyl)-3,3,5-trimethylcyclohexane and hydrated phenol in the presence of an acid catalyst, and then the reaction is continued in the slurry.

BEST MODE FOR CARRYING OUT THE INVENTION

According to the process of the invention for production of 1,1-bis(4-hydroxyphenyl)-3,3,5-trimethylcyclohexane, the reaction of phenol with TMC is started and carried out using an acid catalyst in the presence of hydrated phenol which contains phenol adduct crystals of BPTMC, so that the BPTMC generated in the reaction forms adduct crystals with phenol immediately in the reaction mixture. Thus, the reaction is carried out in a slurry from the start to the completion of the reaction.

In order to start and continue the reaction of phenol with TMC in the presence of an acid catalyst in a slurry which contains phenol adduct crystals of BPTMC as mentioned above, it is preferred that, for example, phenol and water are placed in a reaction vessel before the reaction is started and, while the mixture of phenol and water (i.e., hydrated phenol), which is often referred to the starting liquid mixture, is maintained at a temperature in the range of 15° C. to 40° C. at which phenol adduct crystals of BPTMC do not decompose nor are soluble in the starting liquid mixture, phenol adduct crystals of BPTMC are added to the starting liquid mixture so that phenol adduct crystals of BPTMC are already present in the starting liquid mixture before the start of the reaction. Subsequently an acid catalyst is introduced into the reaction vessel and then a mixture of TMC and phenol to start the reaction while the reaction mixture is maintained at the temperature in the range above mentioned throughout the reaction.

The amount of BPTMC present in the starting liquid mixture before the start of the reaction depends on the temperature of the starting liquid mixture, but it is usually not less than 3% by weight, preferably in the range of 5–15% by weight of the phenol in the starting liquid mixture so that BPTMC readily forms phenol adduct crystals therein.

When phenol is reacted with TMC in the presence of water using an acid catalyst according to the known processes, the generated BPTMC is dissolved in phenol since the reaction mixture contains excess phenol. Accordingly, no adduct crystals are formed throughout the reaction depending on the amount of phenol in the reaction mixture or the temperature of the reaction mixture, or no adduct crystals are formed until the generated BPTMC exceeds its saturation solubility in phenol at the reaction temperature, that is, usually for several hours after the reaction has been started.

In contrast, according to the invention, the reaction of phenol with TMC is started and continued using an acid catalyst in the presence of hydrated phenol which contains phenol adduct crystals of BPTMC. Accordingly, BPTMC generated in the reaction forms adduct crystals with phenol immediately in the reaction mixture so that the reaction is carried out in a slurry from the start of the reaction.

In this manner, the starting liquid mixture is a slurry which contains phenol adduct crystals of BPTMC, and the reaction is started in the slurry according to the invention. Consequently, BPTMC generated by the reaction of phenol with TMC forms phenol adduct crystals immediately in the reaction mixture from the start of the reaction. Thus, BPTMC generated by the reaction of phenol with TMC is excluded as phenol adduct crystals or a solid phase from the liquid phase of the reaction mixture which contains phenol, TMC and water from the start of the reaction. Accordingly, undesired side reactions are suppressed, but also the desired reaction is promoted, and as a result, the selectivity and yield of the reaction improves.

The ratio of phenol (A) and TMC (B) both used as raw materials is in the range of 4 to 9, preferably in the range of 6 to 8, in terms of A/B molar ratio. In addition, aromatic hydrocarbons such as toluene, xylene or mesitylene may be used together with phenol in an amount of 10% by weight or less based on the reaction mixture.

According to the invention, water is used together with phenol usually in an amount of 3–20% by weight, preferably in an amount of 5–15% by weight, based on the amount of phenol used in the reaction. The water serves to form hydrated phenol and hence to lower the freezing point of phenol, and besides, it serves to improve the absorption of hydrogen chloride gas of the reaction mixture when it is used as a catalyst, thereby to increase the reaction velocity.

The acid catalyst used in the invention is mineral acids such as hydrogen chloride gas, concentrated hydrochloric acid, concentrated sulfuric acid, phosphoric acid or methanesulfonic acid. These may be used singly or as a mixture of two or more. Among these mineral acids, hydrogen chloride gas is particularly preferred. On the other hand, phosphoric acid acts not only as an acid catalyst when it is used together with another acid catalyst but also as a pH buffer agent for the reaction mixture. Thus, phosphoric acid may be used together with hydrogen chloride gas.

It is possible to react phenol with TMC by using only a mineral acid as an acid catalyst, but it is preferred to use a thiol as a promoter together with the mineral acid. The use of a promoter accelerates the reaction. Alkyl mercaptans of 1–12 carbons are preferred as the thiol, and as such thiols, there may be mentioned, for example, methyl mercaptan, ethyl mercaptan, n-octyl mercaptan or n-lauryl mercaptan or alkali metal salts such as sodium salts of these alkyl mercaptans. Among these, sodium methyl mercaptide is in particular preferred. The thiol is used usually in an amount of 1–30 mol %, preferably 2–10 mol %, based on TMC used.

When hydrogen chloride gas is used as an acid catalyst, it is preferred that the reaction is carried out in such a manner that the concentration of hydrogen chloride gas in the gas phase in a reaction vessel is in the range of 75–90% by volume so that the yield of the desired reaction product improves, although the reason therefore has not yet been clarified.

In order to maintain the concentration of hydrogen chloride gas in the gas phase in the reaction vessel at 75–90% by volume, the concentration of hydrogen chloride gas is maintained at 75–90% by volume of the total amount (100% by volume) of an inert gas such as nitrogen gas and hydrogen chloride gas in the vapor phase in the reaction vessel under the atmospheric pressure, for example.

It is well known that generally in the reactions in which hydrogen chloride gas is used as a catalyst, the reaction is carried out while the concentration of hydrogen chloride gas in the reaction mixture is maintained at a saturation concentration. In fact, the concentration of hydrogen chloride in the reaction mixture can be easily maintained at the saturation concentration by, for example, introducing 100% by volume dried hydrogen chloride gas into a reaction vessel continuously under the atmospheric pressure. However, according to the invention, the reaction yield improves when the concentration of hydrogen chloride gas in the gas phase in the reaction vessel is adjusted in the range as mentioned above. The reaction yield decreases when hydrogen chloride gas is introduced into a reaction vessel in such high concentrations as about 100% by volume, possibly because a part of BPTMC generated is decomposed under such conditions.

In the process of the invention, the reaction temperature is usually in the range of 15–40° C., preferably in the range of 20–30° C. When the reaction is carried out at the temperature as mentioned above, the phenol adduct crystals of BPTMC formed in the reaction are neither decomposed nor dissolved in the reaction mixture. Further, the reaction is carried out usually under the atmospheric pressure, however, the reaction may be carried out under increased pressures.

The manner in which phenol is reacted with TMC is not specifically limited, however, as mentioned hereinbefore, it is preferred that phenol is reacted with TMC in the following manner. That is, either BPTMC crystals, or at least a part of secondary filtrate residue which is obtained from the secondary crystallization and filtration and contains phenol and BPTMC and, if necessary, a part of primary filtrate which is obtained from the primary crystallization and filtration and contains phenol, BPTMC and by-products such as isomers or polymeric material, as described hereinafter, is added to the starting liquid mixture composed of phenol and water to prepare a slurry containing phenol adduct crystals of BPTMC as described hereinbefore. Hydrogen chloride gas is then introduced into the reaction vessel and the concentration of hydrogen chloride gas in the gas phase is adjusted at 75–90% by volume. In this way, the hydrogen chloride gas is made into contact with the slurry while a mixture of TMC and phenol is added dropwise into the slurry in the reaction vessel to start and continue the reaction.

After the reaction, the resulting reaction mixture in the form of slurry is neutralized with an aqueous solution of an alkali such as sodium hydroxide and is then heated to dissolve phenol adduct crystals of BPTMC in the reaction mixture so that the reaction mixture comes to a solution. Then water is removed from the solution, and the obtained oily substance is cooled to crystallize the desired phenol adduct crystals of BPTMC out of the oily substance (primary crystallization). The phenol adduct crystals of BPTMC are then filtered and separated from the oily substance by suitable means, for example, by centrifugation while a primary filtrate is obtained (primary filtration).

If necessary, the adduct crystals are further purified. For example, a mixed crystallization solvent of aromatic hydrocarbon such as toluene and water is added to the adduct crystals obtained in the primary crystallization and filtration step to dissolve the adduct crystals in the solvent preferably under increased pressure. The resulting solution is then cooled to crystallize BPTMC and collected by filtration to provide high purity BPTMC (secondary crystallization and filtration).

INDUSTRIAL APPLICABILITY

As described above, since the process of the invention for the production of BPTMC by the reaction of phenol with TMC in the presence of an acid catalyst comprises starting the reaction in a slurry which contains phenol adduct crystals of BPTMC and continuing the reaction in the slurry, the process provides BPTMC in high selectivity and in high yield in an industrially stable manner.

EXAMPLES

The invention is described in more detail with reference to examples, but the invention is not limited these examples.

EXAMPLE 1

112.8 g (1.2 mol) of phenol, 16.9 g of water, 0.5 g of 75% aqueous solution of phosphoric acid and 7.2 g of BPTMCP crystals were placed in a one liter capacity four-necked flask provided with a thermometer, a dropping funnel, a reflux condenser and a stirrer to prepare a slurry. The slurry was adjusted at a temperature of 20° C. After the inside the flask was replaced by nitrogen gas, hydrogen chloride gas was introduced into the flask under stirring. The gas composition in the reaction vessel was analyzed and the volume concentration of hydrogen chloride gas was adjusted at 80%.

4.2 g of 15% aqueous solution of sodium methyl mercaptide was added dropwise to the slurry while the slurry was maintained at a temperature of 20° C., and then a mixture of 112.8 g (1.2 mol) of phenol and 42.0 g (0.3 mol) of TMC was added dropwise to the slurry over a period of six hours. The reaction mixture was found to increase in temperature during the addition, and when the addition was completed, the temperature was found to be 40° C. Then, the reaction was further continued at a temperature of 40° C. for anther three hours under stirring until completion. The reaction mixture was found to be slurry throughout the reaction from the start of the reaction when the mixture of phenol and TMC was added dropwise to the slurry to the completion of the reaction The resulting reaction mixture was analyzed by liquid chromatography. The production yield (mol of BPTMC produced/mol of starting TMC used) was found 92.9%.

REFERENCE EXAMPLE 1

After the completion of the reaction described in Example 1, an aqueous solution of sodium hydroxide was added to the reaction mixture in the form of slurry so that it was neutralized. The reaction mixture was then heated to come to a solution and the solution was cooled to crystallize phenol adduct crystals of BPTMC out of the solution and the adduct crystals were collected by filtration (primary crystallization and filtration).

Then, a mixed solvent of toluene and water was added to the adduct crystals, and the mixture was heated so that the adduct crystals were dissolved in the solvent. After removing water and cooling, the resulting purified crystals of BPTMC were collected by filtration (secondary crystallization and filtration).

The resulting secondary filtrate obtained by the secondary filtration was subjected to distillation to recover the toluene used as the crystallization solvent while 38.5 g of distillation residue (secondary filtrate residue) containing 25.3 g (0.27 mol) of phenol and 12.8 g (0.04 mol) of BPTMC was obtained.

EXAMPLE 2

The volume concentration of hydrogen chloride gas in the gas phase in the reaction vessel was adjusted at 90%, and otherwise in the same manner as in Example 1, the reaction was carried out. As a result, the production yield of BPTMC was found to be 89.0%.

EXAMPLE 3

87.5 g (0.93 mol) of phenol, 16.9 g of water and 38.5 g of the distillation residue (secondary filtrate residue) which had been obtained in Reference Example 1 were placed in a one liter capacity four-necked flask provided with a thermometer, a dropping funnel, a reflux condenser and a stirrer to prepare a slurry containing phenol adduct crystals of BPTMC.

The slurry was adjusted at a temperature of 20° C. After the inside the flask was replaced by nitrogen gas, hydrogen chloride gas was introduced into the flask under stirring. The gas composition in the reaction vessel was analyzed and the volume concentration of hydrogen chloride gas was adjusted at 70%.

4.2 g of 15% aqueous solution of sodium methyl mercaptide was added dropwise to the slurry while the slurry was maintained at a temperature of 20° C., and then a mixture of 112.8 g (1.2 mol) of phenol and 42.0 g (0.3 mol) of TMC was added dropwise to the slurry over a period of nine hours. The reaction mixture was found to increase in temperature during the addition, and when the addition was completed, the temperature was found to be 40° C. Then, the reaction was further continued for anther half an hour. The reaction mixture was found to be slurry throughout the reaction from the start of the reaction when the mixture of phenol and TMC was added dropwise to the slurry to the completion of the reaction The resulting reaction mixture was analyzed by liquid chromatography. The production yield (mol of BPTMC produced/mol of starting TMC used) was found to be 92.2%.

COMPARATIVE EXAMPLE 1

112.8 g (1.2 mol) of phenol was used while the distillation residue (secondary filtrate residue) obtained in Reference Example 1 was not used, and otherwise in the same manner as in Example 3, the reaction was carried out. The reaction mixture was found to be solution when the reaction was started (i.e., when the dropwise addition of a mixture of phenol and TMC was started), but after three hours from the start of the reaction, the reaction mixture was found to be slurry on account of phenol adducts of BPTMC generated in the reaction mixture.

The resulting reaction mixture was analyzed by liquid chromatography. The production yield of BPTMC was found to be 77.9%.

COMPARATIVE EXAMPLE 2

The volume concentration of hydrogen chloride gas in the gas phase in the reaction vessel was adjusted at 97%, and otherwise in the same manner as in Example 1, the reaction was carried out. As a result, the production yield of BPTMC was found to be 80.3%.

COMPARATIVE EXAMPLE 3

The volume concentration of hydrogen chloride gas in the gas phase in the reaction vessel was adjusted at 60%, and otherwise in the same manner as in Example 1, the reaction was carried out. As a result, the production yield of BPTMC was found to be 82.9%.

What is claimed is:

1. A process for production of 1,1-bis(4-hydroxyphenyl)-3,3,5-trimethylcyclohexane which comprises reacting phenol with 3,3,5-trimethylcyclohexanone in the presence of an acid catalyst wherein the reaction of phenol with 3,3,5-trimethylcyclohexanone is started in a slurry comprising phenol adduct crystals of 1,1-bis(4-hydroxyphenyl)-3,3,5-trimethylcyclohexane and hydrated phenol in the presence of an acid catalyst, and then the reaction is continued in the slurry.

2. The process as claimed in claim 1 wherein hydrogen chloride gas is used as an acid catalyst, and the reaction is carried out under hydrogen chloride gas of the concentration of 75–90% by volume in the gas phase in a reaction vessel.

3. The process as claimed in claim 1 wherein the reaction is carried out at a temperature of 15–40° C.

* * * * *